United States Patent [19]

Kauth et al.

[11] Patent Number: 4,701,554

[45] Date of Patent: Oct. 20, 1987

[54] PROCESS FOR THE PREPARATION OF POLYPHOSPHONIC ACID AMIDES

[75] Inventors: Hermann Kauth; Manfred Schmidt; Dieter Freitag; Udo Rudolph, all of Krefeld; Frank Kleiner, Leverkusen, all of Fed. Rep. of Germany

[73] Assignee: Bayer Aktiengesellschaft, Leverkusen, Fed. Rep. of Germany

[21] Appl. No.: 807,348

[22] Filed: Dec. 10, 1985

Related U.S. Application Data

[63] Continuation of Ser. No. 671,202, Nov. 14, 1984, abandoned.

[30] Foreign Application Priority Data

Nov. 25, 1983 [DE] Fed. Rep. of Germany ....... 3442637

[51] Int. Cl.$^4$ ............................ C07F 9/44; C07F 9/65
[52] U.S. Cl. ..................................... 564/14; 528/398; 544/337
[58] Field of Search ......................... 564/14; 528/398; 558/138; 544/337

[56] References Cited

U.S. PATENT DOCUMENTS

| | | | |
|---|---|---|---|
| 3,253,063 | 5/1966 | Nielsen | 558/138 |
| 3,377,409 | 4/1968 | McConnell et al. | 528/398 |
| 3,450,677 | 6/1969 | McConnell et al. | |
| 4,152,373 | 5/1979 | Honig et al. | |
| 4,403,075 | 9/1983 | Byrd et al. | |

FOREIGN PATENT DOCUMENTS 1167050  11/1958  France .

Primary Examiner—Anton H. Sutto
Attorney, Agent, or Firm—Connolly & Hutz

[57] ABSTRACT

The invention relates to a process for the preparation of polyphosphonic acid amides by condensation of 0.5-2 moles of a phosphonic acid diaryl ester and 1 mole of an aliphatic, aromatic, araliphatic or heterocyclic primary or secondary diamine in the melt at 50°-350° C., if appropriate in the presence of a catalyst which accelerates the condensation and under an inert gas atmosphere, the corresponding phenol being split off.

8 Claims, No Drawings

PROCESS FOR THE PREPARATION OF POLYPHOSPHONIC ACID AMIDES

This application is a continuation of application Ser. No. 671,202 filed Nov. 14, 1984 now abandoned.

The present invention relates to a process for the preparation of polyphosphonic acid amides.

It is already known that polymers can be prepared from dialkylamino-phosphonic acid amides and alkyl- or aryl-polyamines (compare, for example, U.S. Pat. No. 3,546,141). The reaction of phosphonic acid dichlorides with diamines has also been described (compare, for example, Harris et al. J. Polymer Science 35, 540 (1959)). Polyphosphonic acid amides are furthermore accessible from phosphonic acid bisimidazolides and diamines (compare, for example, U.S. Pat. No. 3,244,647). The disadvantage of the first process is the formation of hydrogen halide or amine hydrochloride, which can be removed only with difficulty. In addition, a residual content of hydrolysable chlorine in the polymer cannot always be prevented, which in turn causes corrosion during industrial processing.

Phosphonic acid imidazolides and amides are comparatively expensive starting compounds which require a relatively large effort and must first be synthesised from the corresponding phosphonic acid dichlorides.

Attempts to react phosphonic acid esters with diamines to give polyphosphonic acid amides by splitting off the hydroxyl component on which the ester is based have not hitherto been disclosed. In this context, M. Sander and E. Steininger in J. of Macromolecular Science-Reviews in Macromolecular Chemistry, Volume C 1, No. 1 (1967), page 128, lines 1 to 2 state: Diamines and phosphonic acid esters do not give polyphosphonic acid amides.

It has now been found, surprisingly, that polymers with recurring units of the general formula I

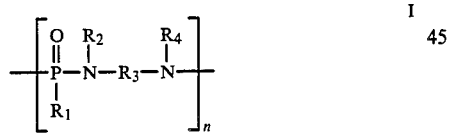

can be prepared if diamines of the general formula II

and phosphonic acid esters of the general formula III

wherein, in the formulae I to III:

$R_1$ denotes $C_1$–$C_6$-alkyl, $C_6$–$C_{15}$-aryl, $C_2$–$C_{12}$-alkenyl, $C_7$–$C_{18}$-alkylaryl or $C_7$–$C_{18}$-aralkyl;

$R_3$ denotes one or more radicals chosen from $C_2$–$C_{12}$-alkylene; phenylene

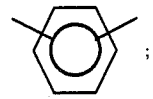

bisphenylene

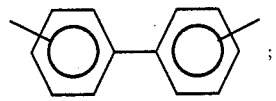

alkylene-bisphenylene

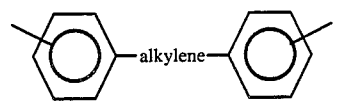

where alkylene=$C_1$–$C_4$-alkylene, $C_2$–$C_4$-alkylidene, $C_5$–$C_{12}$-cycloalkylene or $C_6$–$C_{12}$-cycloalkylidene; thiobisphenylene

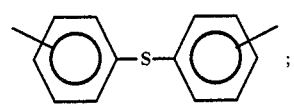

oxybisphenylene

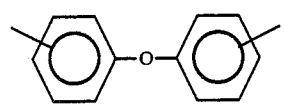

sulphonyl-bisphenylene

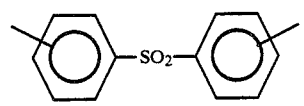

carbonyl-bisphenylene

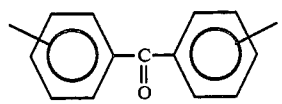

and bis(alkylene)-phenylene

with 1–4 C atoms in each alkylene group, it being possible for each of the phenyl nuclei of the $R_1$ and $R_3$ radicals to be substituted by 1–4 $C_1$–$C_4$-alkyl groups or 1–4 halogen atoms (Cl, Br) or by the alkyl groups and halogen atoms mentioned, $R_2$=$R_4$ and these radicals denote hydrogen or $C_1$–$C_4$-alkyl, or $R_2$ and $R_4$ together denote an alkylene group which has 1-6 C atoms and links the two nitrogen atoms, in which case $R_3$ is restricted to alkylene with 2-6 C atoms;

Ar denotes phenyl or cresyl and n denotes 3-20, are subjected to a condensation reaction in the melt at 50°-350° C., the phenol or cresol split off being distilled off, 0.5-2 moles of the phosphonic acid ester of the formula III being used per mole of the diamine of the formula II and the reaction being carried out, if appropriate, in an oxygen-free inert gas atmosphere and, if appropriate, in the presence of $10^{-5}$ to $10^{-1}$ mol %, based on 100 mol % of diamine, of a catalyst which accelerates the condensation.

Preferably, in the formulae I to III:

$R_1$ denotes methyl or phenyl, in particular methyl;

$R_2$ and $R_4$ denote hydrogen; or $R_2$ and $R_4$ together denote a —CH$_2$—CH$_2$—CH$_2$— group, in which case $R_3$ is restricted to a —CH$_2$—CH$_2$— group;

$R_3$ denotes at least one of the radicals $C_2$-$C_6$-alkylene; phenylene

alkylenebisphenylene

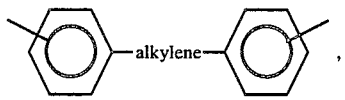

where alkylene=$C_1$-$C_4$-alkylene, in particular $C_1$-$C_2$-alkylene, $C_2$-$C_4$-alkylidene, in particular isopropylidene; cyclohexylene; or cyclohexylidene; or xylylene

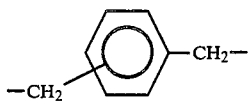

it being possible for each phenyl nucleus of $R_1$ and $R_3$ to be substituted by 1 or 2 $C_1$-$C_4$-alkyl radicals, in particular methyl;

Ar denotes phenyl and n=3-15.

The phosphonic acid diaryl ester and diamine can be used in a molar ratio of between 1:2 and 2:1, preferably in an approximately equimolar ratio, for the process according to the invention.

It may be advantageous to meter in the diamine component successively during the reaction.

The temperature range in which the process according to the invention is carried out depends greatly on the nature of the diamine employed. It varies between 50° C. and 350° C., 100°-250° C. being preferred for aliphatic diamines and 150°-320° C. being preferred for aromatic or aromatic-aliphatic diamines.

The process according to the invention can also advantageously be carried out under an oxygen-free inert gas atmosphere, for example under nitrogen or a noble gas, preferably nitrogen.

Furthermore, catalysts can be added in the process according to the invention in order to accelerate the condensation.

Examples of such catalysts are: sodium hydride, sodium amide, sodium borohydride and sodium alcoholates, such as NaOCH$_3$, NaOC$_2$H$_5$ and sodium phenolate; titanium tetrabutylate, zinc acetate, vanadyl triethylate, zirconium tetrapropylate, dibutyltin diacetate and dibutyltin dimethylate; and p-toluenesulphonic acid.

Although aliphatic diamines as a rule react without a catalyst, catalysts can be used to increase the rate of reaction. If the aromatic or aliphatic-aromatic diamines are used, basic or strongly basic catalysts, such as alkali metal alcoholates, alkali metal phenolates and alkali metal hydrides, are preferably employed.

The amounts of catalysts which are employed, if appropriate, are $10^{-5}$ to $10^{-1}$ mol %, preferably $10^{-4}$ to $10^{-2}$ mol %, based on 100 mol % of diamine.

In carrying out the process according to the invention, 1 mole of phenol or cresol is theoretically split off per amino group, and is removed from the reaction mixture by distillation under reduced pressure (finally under about 0.5-5 mbar).

At the end of the reaction—recognisable from the amount of phenol (cresol) split off—free, unreacted amino end groups can be masked by reaction in a known manner with an amount at least equivalent to the amino end groups of a substance chosen from the following classes: monocarboxylic acid chlorides, such as, for example, acetyl chloride or benzoyl chloride, carboxylic acid anhydrides, such as, for example, phthalic anhydride or maleic anhydride, monoisocyanates, such as for example, phenyl, benzyl, naphthyl or stearyl isocyanate, and carbonates, such as, for example, diphenyl carbonate or diethyl carbonate.

Polymers which can be animolysed, such as, for example, polybutylene terephthalate, polyethylene terephthalate and polycarbonate, are also suitable for reaction with the amino end groups which have not reacted. Monoisocyanates or carboxylic acid anhydrides are preferably used.

For isolation of the product, the viscous polyphosphonic acid amide is drained out of the reaction vessel and is comminuted by means of suitable apparatuses, such as, for example, cooling rolls, mills, granulators and the like, to particles of a size which can be handled industrially.

The percentages given in the examples relate to the weight, unless indicated otherwise.

EXAMPLE 1

7,440 g (30 moles) methanephosphonic acid diphenyl ester, 4,080 g (30 moles) of m-xylylenediamine and 0.3 g ($7.7\times10^{-3}$ moles) of sodium amide are mixed intensively in an autoclave under nitrogen at 220° C. The mixture is stirred at this temperature under atmospheric pressure for 2 hours and phenol is then distilled off over a column, heated to 130° C., under a vacuum falling from 350 to 100 mbar and at a temperature rising to 240° C. in the course of 3 hours. The reaction is subsequently continued at 240° C. for 4 hours, under a pressure which is gradually reduced to ~1 mbar. The autoclave is gassed with nitrogen and the product is allowed to settle and is isolated by draining and comminution via a cooling roll. The polyphosphonic acid amide is soluble in methanol, cresol, glacial acetic acid and dimethylsulphoxide but insoluble in methylene chloride and has the following properties: Viscosity $\eta_{rel}=1.14$ (1 g of substance per 100 ml of solution; solvent: m-cresol)

Glass transition temperature $T_g=78°$ C.

Average molecular weight (number-average) $\overline{MW}_{osm.}=1,500$

Yield: 5,700 g.

The IR spectrum of the polyphosphonic acid amide obtained is virtually identical with that of a polyphosphonic acid amide prepared from 1 mole of methanephosphonic acid dichloride and 1 mole of m-xylylenediamine.

EXAMPLE 2

138,6 g (0.7 mole) of 4,4'-diaminodiphenylmethane are added dropwise to 191 g (0.77 mole) of methanephosphonic acid diphenyl ester at 240° C. under 140 mbar in the course of 2.5 hours. The reaction is catalysed with 50 mg ($1.3 \times 10^{-3}$ mole) of sodium amide. During the dropwise addition, phenol is distilled off over a column heated to 130° C. The reaction is then continued at a temperature of 240° C. under a vacuum which is gradually reduced to 5 mbar for 9 hours.

Unreacted monomer is distilled off, without a column, under 1 mbar and a polyphosphonic acid amide which is soluble in methanol, cresol, dimethylformamide, glacial acetic acid and dimethyl sulphoxide but insoluble in water and methylene chloride and has the following properties is obtained:

Amino end groups: 1.2%

Viscosity $\eta_{rel}=1.09$ (1 g of substance per 100 ml of solution; solvent: m-cresol)

Glass transition temperature $T_g=110°$ C.

Average molecular weight (number-average) $\overline{MW}_{osm.}=800$

Yield: 185 g

The IR spectrum of the product thus prepared is essentially identical to that given by the reaction product of 0.1 mole of 4,4'-diaminodiphenylmethane and 0.11 mole of methanephosphonic acid dichloride.

EXAMPLE 3

136 g (1 mole) of m-xylylenediamine and 248 g (1 mole) of methanephosphonic acid diphenyl ester are subjected to melt condensation, without sodium amide as a catalyst, by a procedure analogous to that described in Example 1. A polyphosphonic acid amide with the following properties is obtained:

Viscosity $\eta_{rel}=1.15$ (1 g of substance per 100 ml of solution; solvent: m-cresol)

Glass transition temperature $T_g=93°$ C.

Average molecular weight (number-average) $\overline{MW}_{osm.}=1,800$ yield: 150 g.

The IR spectrum of the polyphosphonic acid amide obtained is essentially identical to that given by the reaction product of 0.1 mole of xylylenediamine with 0.1 mole of methanephosphonic acid dichloride.

EXAMPLE 4

190.4 g (1.4 moles) of m-xylylenediamine and 173.6 g (0.7 mole) of methanephosphonic acid diphenyl ester are stirred under nitrogen at 220° C. for two hours, without sodium amide as a catalyst. Thereafter, a mixture of xylylenediamine and phenol is distilled off at 240° C. under a vacuum which is reduced to 20 mbar in the course of 9 hours and then under a high vacuum of about 3 mbar.

176 g of a polymer with the following properties are obtained:

Viscosity $\eta_{rel}=1.22$ (1 g of substance per 100 ml of solution; solvent: m-cresol)

Glass transition temperature $T_g=88°$ C.

Average molecular weight (number-average) $\overline{MW}_{osm.}=2,300$

EXAMPLE 5

99 g (0.5 mole) of 4,4'-diaminodiphenylmethane are added dropwise to 248 g (1 mole) of methanephosphonic acid diphenyl ester at 240° C. under 150 mbar in the course of one hour. The reaction is catalysed with 50 mg of NaNH$_2$. During the dropwise addition, phenol is distilled off over a column. The reaction is then continued at a temperature of 240° C. under a vacuum which is reduced to about 1 mbar in the course of 6 hours. The column is removed and unreacted starting ester is distilled off to give 185 g of an oligomer with the following properties: Amino end groups: 0.3%

Viscosity $\eta_{rel}=1.1$ (1 g of substance per 100 ml of solution; solvent: m-cresol)

Glass transition temperature $T_g=120°$ C.

Average molecular weight (number-average) $\overline{MW}_{osm.}=950$

The following comparison example shows that phosphonic acid dialkyl esters and aromatic diamines do not react with splitting-off of alcohol, from which it may be concluded that no polyphosphonic acid amide formation takes place.

COMPARISON EXAMPLE 0.5 mole (62 g) of methanephosphonic acid dimethyl ester and 0.5 mole (99 g) of 4,4'-diaminodiphenylmethane are brought together under nitrogen and the mixture is slowly heated to 150° to 170° C. An exothermic reaction takes place here. Subsequent distillation gives a substance mixture which contains virtually no methanol, which rather indicates a transformation of the 4,4'-diaminodiphenylmethane.

We claim:

1. A process for the production of a polymer with recurring units of the general formula

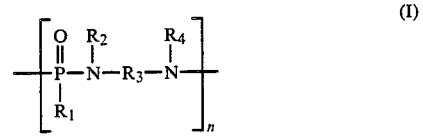

(I)

in which a diamine of the general formula

(II)

and a phosphonic acid ester of the general formula

(III)

in which, in the formulae (I) to (III):

$R_1$ denotes $C_1$–$C_6$-alkyl, $C_6$–$C_{15}$-aryl, $C_2$–$C_{12}$-alkenyl, $C_7$–$C_{18}$-alkylaryl or $C_7$–$C_{18}$-aralkyl;

$R_3$ denotes one or more radicals chosen from $C_2$–$C_{12}$-alkylene; phenylene

bisphenylene

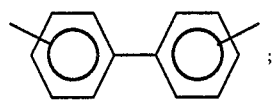

alkylene-bisphenylene

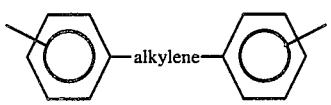

where
"alkylene" = $C_1$–$C_4$-alkylene, $C_2$–$C_4$-alkylidene, $C_5$–$C_{12}$-cycloalkylene or $C_6$–$C_{12}$-cycloalkylidene; thiobisphenylene

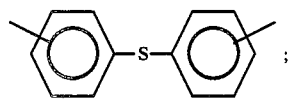

oxybisphenylene

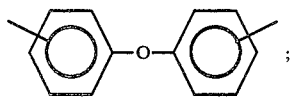

sulphonyl-bisphenylene

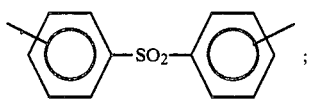

carbonyl-bisphenylene

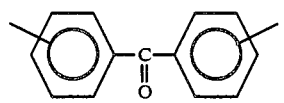

and bis(alkylene)-phenylene

with 1 to 4 carbon atoms in each alkylene group; each of the phenyl nuclei of the $R_1$ and $R_3$ radicals being optionally substituted by substituents selected from 1 to 4 $C_1$–$C_4$-alkyl groups and 1 to 4 halogen atoms (Cl, Br), $R_2 = R_4$ and these radicals denote hydrogen or $C_1$–$C_4$-alkyl, or $R_2$ and $R_4$ together denote an alkylene group which has 1 to 6 carbon atoms and links the two nitrogen atoms, in which case $R_3$ is restricted to alkylene with 2 to 6 carbon atoms;

Ar denotes phenyl or cresyl and n is 3 to 20, inclusive, are subjected to a condensation reaction with a basic catalyst in the melt at 50° to 350° C., the phenol or cresol split off being distilled off, 0.5 to 2 moles of the phosphonic acid ester of the formula (III) being used per mole of the diamine of the formula (II).

2. A process according to claim 1 in which the reaction is carried out in an oxygen-free inert gas atmosphere.

3. A process according to claim 1 in which the reaction is carried out in the presence of $10^{-5}$ to $10^{-1}$ mol %, based on 100 mol % of diamine, of a catalyst which accelerates the condensation.

4. A process according to claim 3 in which the reaction is carried out in the presence of $10^{-4}$ to $10^{-2}$ mol %, based on 100 mol % of diamine, of a catalyst which accelerates the condensation.

5. A process according to claim 3 in which the catalyst is selected from sodium hydride, sodium amide, sodium borohydride, sodium methoxide, sodium ethoxide, sodium phenolate, titanium tetrabutylate, zinc acetate, vanadyl triethylate, zirconium tetrapropylate, dibutyltin diacetate, dibutyltin dimethylate and p-toluenesulphonic acid.

6. A process according to claim 3, in which, in the formulae (I) to (III)

$R_1$ denotes methyl or phenyl, $R_2$ and $R_4$ denote hydrogen; or $R_2$ and $R_4$ together denote a —$CH_2$—$CH_2$—group, in which case $R_3$ is restricted to a —$CH_2$—$CH_2$— group;

$R_3$ denotes at least one of the radicals $C_2$–$C_6$-alkylene; phenylene

alkylenebisphenylene

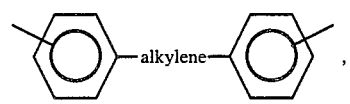

where
"alkylene" = $C_1$–$C_2$alkylene, isopropylidene, cyclohexylene, or cyclohexylidene; or xylylene

it being possible for each phenyl nucleus of $R_1$ and $R_3$ to be substituted by 1 or 2 methyl radicals;

Ar denotes phenyl and n is 3 to 15, inclusive.

7. A process according to claim 3 in which $R^1$ denotes methyl and Ar denotes phenyl.

8. A process according to of claim 3 in which the reaction is carried out at a temperature between 100° to 250° C. if the diamine of formula (II) is an aliphatic diamine or at a temperature between 150° and 320° C. if the diamine of formula (II) is an aromatic or aromatic-aliphatic diamine.

* * * * *